United States Patent
Borgne-Sanchez et al.

(10) Patent No.: US 8,809,346 B2
(45) Date of Patent: Aug. 19, 2014

(54) ANT-LIGANDS MOLECULES AND BIOLOGICAL APPLICATIONS

(75) Inventors: Annie Borgne-Sanchez, Paris (FR); Etienne Jacotot, Paris (FR); Catherine Brenner, Le Chesnay (FR)

(73) Assignees: Universite de Versailles-Saint-Quentin-en-Yvelines, Versailles Cedex (FR); Center National de la Recherche Scientifique (CNRS), Paris Cedex (FR); Mitologics, Romainville (FR)

( * ) Notice: Subject to any disclaimer, the term of this patent is extended or adjusted under 35 U.S.C. 154(b) by 490 days.

(21) Appl. No.: 12/995,361

(22) PCT Filed: May 29, 2009

(86) PCT No.: PCT/IB2009/006076
§ 371 (c)(1),
(2), (4) Date: Nov. 30, 2010

(87) PCT Pub. No.: WO2009/144584
PCT Pub. Date: Mar. 12, 2009

(65) Prior Publication Data
US 2011/0086865 A1    Apr. 14, 2011

Related U.S. Application Data

(60) Provisional application No. 61/057,350, filed on May 30, 2008.

(51) Int. Cl.
A01N 43/90 (2006.01)
A61K 31/519 (2006.01)
C07D 491/00 (2006.01)
C07D 495/00 (2006.01)

(52) U.S. Cl.
USPC ........................................ 514/260.1; 544/278

(58) Field of Classification Search
None
See application file for complete search history.

(56) References Cited

U.S. PATENT DOCUMENTS

| | | | | |
|---|---|---|---|---|
| 4,376,121 | A * | 3/1983 | Kienzle | ............ 514/267 |
| 2004/0198777 | A1 | 10/2004 | Ghosh et al. | |
| 2005/0038051 | A1 | 2/2005 | Nunnari et al. | |

FOREIGN PATENT DOCUMENTS

| | | | | |
|---|---|---|---|---|
| EP | 276825 | A | 8/1988 | |
| WO | WO97/02262 | * | 1/1997 | ........... C07D 401/12 |
| WO | 2004058704 | A | 7/2004 | |
| WO | 2004101506 | A | 11/2004 | |
| WO | 2008/045406 | A | 4/2008 | |
| WO | 2008052441 | A | 5/2008 | |

OTHER PUBLICATIONS

Ivachtchenko, et. al., Journal of Combinatorial Chemistry (2004), 6(4), 573-583.*
Kovalenko, et. al., Zhurnal Organichnoi ta Farmatsevtichnoi Khimii (2007), 5(3), 34-40.*
Smolanka, et. al., Ukrainskii Khimicheskii Zhurnal (Russian Edition) (1973), 39(4), 402-3.*
Sauter, et. al., Monatsh. Chem. (1973), 104(6), 1593-8.*
International Patent Application No. PCT/IB2009/006076, International Preliminary Report on Patentability dated Dec. 9, 2010, 12 pages.
Khalil, Ashraf A. et al., "Substituted Quinazolines, Part 2, Synthesis and in-vitro anticancer evaluation of new 2-substituted mercapto-3H-quinazoline analogs," Archiv Der Pharmazie, Weinheim, Germany, 336(2), 95-103 Coden: Arpmas; ISSN: 0365-6233, 2003, XP002545266.
Database Registry, Chemical Library Supplier: ChemDiv, Inc 2, Jun. 2, 2004, XP002545267 retrieved from STN accession No. 688344-90-3.
Database Registry, Chemical Library Supplier: Aurora Fine Chemicals, Jul. 28, 2006, XP002545268 retrieved from STN accession No. 896797-03-8.
Database Registry, Chemical Library Supplier: CehmDiv, Inc., Jun. 2, 2004, XP002545268 retrieved from STN accession No. 688340-73-0.
Database Registry, Chemical Library Supplier: ChemDiv, Inc., Jun. 2, 2004, XP002545270 retrieved from STN accession No. 688341-01-7.
Database Registry, Chemical Library Supplier: Chem Lib. Suppl.: Princeton Biomolecular R, Inc 17, Jul. 17, 2006, XP002545271 retrieved from STN accession No. 893686-46-9.

* cited by examiner

*Primary Examiner* — Jeffrey H Murray
(74) *Attorney, Agent, or Firm* — Conley Rose, P.C.

(57) ABSTRACT

The invention relates to molecules ANT-ligands having a substituted nitrogeneous heterocycle A wherein
A is a substituted pyrazinone of formula I

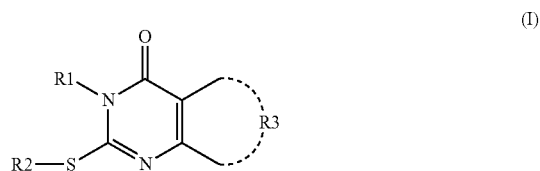

wherein
R1 is
—$(CH_2)_n$—CO—OH;
—$(CH_2)_n$—CO—OR;
—$(CH_2)_n$—CO—NHR;
—$(CH_2)_n$—CO—N(R,R');
—$(CH_2)_n$—OH;
—$(CH_2)_n$—OR;
—$(CH_2)_n$—OAr;
—$(CH_2)_n$—C(R,R')—$(CH_2)_n$—OH,
R and R', in the above radicals, being identical or different and representing H or a C1-C12 alkyl or cycloalkyl radical; and Ar is a phenyl or Het., Het. representing an heterocyclic radical with one or several hetero atoms selected between N, S and O, said phenyl or heterocycle being optionally substituted by one or several atoms, groups or radicals selected from halogen atoms such as Cl, Br, I, or halogenated groups such as —CCl₃ or —CF₃; one or several —OH, —OR, —COOH or —COOR groups; a phenyl; a linear or branched C1-C12 alkyl radical; —NH—COR; or —CN; said groups occupying the same or different positions on the phenyl or heterocyclic radical;

Figure 1:
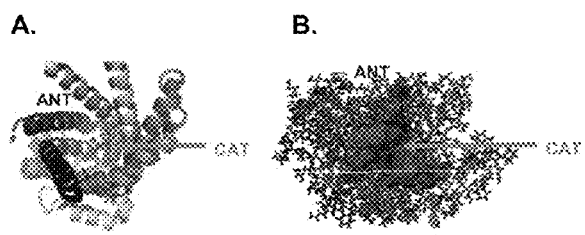

a linear or branched C1-C12 alkyl radical;
a linear or branched C2-C12 alkylene radical;
—$(CH_2)_n$—C3-C6 cycloalkyl radical;
—$(CH_2)_n$Ar or —$(CH_2)_n$Het.;
—$(CH_2)_n$—NH—CO—R;
—$(CH_2)_n$—NH$_2$;
—$(CH_2)_n$—N(R,R');
—$(CH_2)_n$—NH—CO—OH;
—$(CH_2)_n$—NH—CO—OR;
—NH—$(CH_2)_n$—CO—OH;
—NH—$(CH_2)_n$—CO—OR;

R2 is
—$(CH_2)_n$—Ar, Ar being such as above defined and being optionally substituted such as above defined;
a linear or branched C1-C12 alkyl or C2-C12 alkylene radical with one or several double bonds;
—$(CH_2)_n$—OH;
—$(CH_2)_n$—OR;
—$(CH_2)_n$—CO—Het;
—$(CH_2)_n$—NH—CO—R;
—$(CH_2)_n$—NH$_2$;
—$(CH_2)_n$—N(R,R');
—$(CH_2)_n$—CO—OH;
—$(CH_2)_n$—CO—OR;
a linear or branched C1-C12 alkyl radical;
—$(CH_2)_n$—C(R)=CH—C(R)=CH$_2$, R3 forms a phenyl or an heterocyclic condensed group with the two adjacent carbons of the pyrazinone residue, said condensed group being optionally substituted such as above defined for Ar and Het.; and/or condensed to a cyclohexyl or oxanyl group, in turn optionally substituted such as above defined for Ar;

n is 0 or an integer from 1 to 5; or

A is a substituted pyrazine of formula II

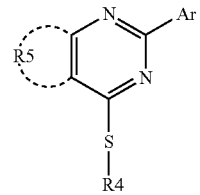

(II)

wherein
$R_4$ is a —CO—NH—Ar radical, optionally substituted such as above defined;
R5 forms a phenyl or heterocyclic group condensed to the two adjacent carbon groups of the pyrazine residue, said phenyl or heterocyclic group being optionally substituted such as above defined, and
Ar being such as above defined with respect to formula I or
A is a substituted pyridine group of formula III

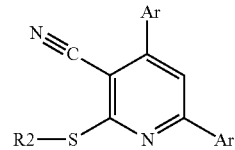

(III)

wherein,
Ar and R2 are as above defined with respect to formula I.

1 Claim, 4 Drawing Sheets

A.
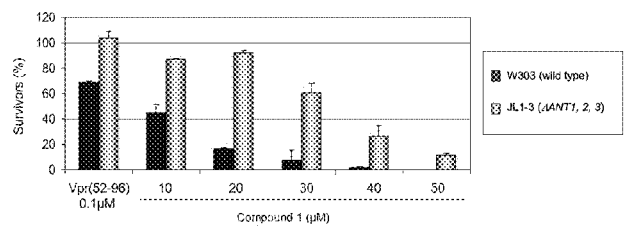
B.
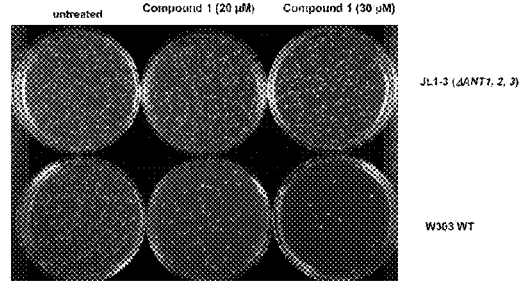
Fig. 5
| | MTT | | | ANT | | MitoTrust | | Yeast | |
|---|---|---|---|---|---|---|---|---|---|
| | LD50 (µM) | | | IC50 (µM) | | Liver (µM) | | ED50 (µM) | |
| Compound | HT-29 | BxPC3 | MiaPaca | WI-38 | Liver | HT-29 | DS50 | DP50 | W303 | JL1-3 |
| Compound 1 | 42.06 | 18.14 | ND | >100 | 23.19 | 22.84 | >200 | >200 | 17.18 | 31.36 |
| Compound 2 | 0.83 | 0.59 | ND | 6.3 | 159.8 | 13.93 | ND | 11.27 | >100 | >100 |
| Compound 3 | 0.87 | 0.53 | 0.69 | 2.50 | 28.69 | 24.03 | >200 | 173 | 16.9 | 35.46 |
| Compound 4 | 0.62 | 0.48 | 0.95 | 100.00 | >100 | 10.23 | ND | 33.60 | ND | ND |
| Compound 5 | <0.2 | <0.2 | 0.24 | 80.63 | >100 | 14.05 | >200 | >200 | >50 | >50 |
| Compound 6 | 1.36 | 0.70 | 1.67 | 93.47 | >100 | 32.19 | 84.65 | >200 | 125 | >200 |
| Compound 7 | 5.71 | 2.57 | 5.87 | 100.00 | 16.94 | 5.09 | >200 | 72.70 | 9.5 | 46.18 |
| Compound 8 | 0.87 | 0.31 | 0.61 | 12.50 | 15.53 | 11.11 | >200 | 132.69 | 8.75 | 17.38 |
| Compound 9 | 0.38 | 0.12 | 0.29 | ND | 22.23 | 16.08 | >200 | 75.25 | 21.34 | >35 |
| Compound 10 | 28.77 | 58.51 | 55.07 | 100.00 | 9.31 | 2.94 | 8.97 | 5.50 | >50 | >50 |
| Compound 11 | 0.87 | 0.53 | 0.73 | 43.91 | >200 | 31.39 | >200 | >200 | 25 | >100 |
| Compound 12 | 3.50 | 0.94 | 1.07 | 10.07 | 27.06 | 56.67 | 19.66 | 5.97 | 3.54 | 6.82 |
| Compound 13 | 1.70 | 1.61 | 1.89 | 52.34 | 28.63 | 26.74 | >200 | 8.62 | 20.53 | 42.88 |
| Compound 14 | 8.76 | 3.69 | 7.33 | >100 | 7.18 | 6.65 | 23.83 | >200 | 3.97 | 9.53 |
| Compound 15 | 5.39 | 3.16 | 4.86 | ND | 8.53 | 8.05 | 66.58 | 16.74 | ND | ND |
| Compound 16 | 4.62 | 2.82 | 4.65 | ND | 6.78 | 13.7 | 120.22 | 57.82 | ND | ND |
Fig. 6

| Compound | MTT DL50 (µM) | | | | ANT IC50 (µM) | | Mitotrust foie | |
|---|---|---|---|---|---|---|---|---|
| | HT-29 | Mia Paca | BxPC3 | WI-38 | Foie | HT-29 | DS50 (µM) | DP50 (µM) |
| 17 | 39,90 | 83,42 | 43,7 | >100 | 22,58 | 9,66 | 18 | 22,77 |
| 18 | 26,20 | 41,31 | 55,9 | >100 | 5,05 | 6,61 | 133,48 | 18,68 |
| 19 | 39,90 | 67,10 | 43,7 | 91,2 | 6,96 | 33,97 | ND | 3,68 |
| 20 | 35,93 | 57,63 | 22,3 | 93,7 | 16,65 | 7,09 | >200 | 79,53 |
| 21 | 39,51 | 68,13 | 6,7 | 100,0 | 17,3 | 22,33 | >200 | >200 |

ANT-LIGANDS MOLECULES AND BIOLOGICAL APPLICATIONS

CROSS-REFERENCE TO RELATED APPLICATIONS

The present application is the U.S. national stage of international patent application number PCT/IB2009/006076, filed May 29, 2009, and claims the benefit thereof under 35 U.S.C. §119(a) and 35 U.S.C. §365(a). PCT/IB2009/006076 claims priority of U.S. Provisional Patent Application No. 61/057,350 filed May 30, 2008. The disclosures of those applications are hereby incorporated herein by reference.

BACKGROUND

The invention relates to molecules having ANT-ligands properties.

It more particularly relates to molecules useful for inducing apoptosis or similar cell death mechanisms and their use as therapeutical agents.

Since ten years ago, the mitochondrion has been progressively recognized as an integrator-coordinator of apoptosis and a major checkpoint leading, upon activation, irreversibly to a regulated cell death process, namely mitochondrial apoptosis. This process is favoured by a sustained $Ca^{2+}$ accumulation in the mitochondrial matrix and manifests as signs of pro-apoptotic mitochondrial alteration, namely permeability transition, dissipation of the electrochemical potential, matrix swelling, cristae remodelling, relocalization of Bax to mitochondria and the release of pro-apoptotic factors such as cytochrome c and AIF from mitochondria. Depending on the physiopathological models, mitochondrial membrane permeabilization (MMP) would affect the outer mitochondrial membrane or both membranes, i.e. the outer and the inner membrane. MMP is under the control of Bax and Bcl-2 family members, which are respectively pro- and anti-apoptotic. Thus, apoptosis can be inhibited by overexpression of oncogenes (e.g. Bcl-2) or viral proteins (e.g. Vmia from Herpes virus). MMP is usually accompanied by a bioenergetic catastrophe: a loss of transmembrane potential ($\Delta\psi_m$), an arrest of respiration, a decrease in ATP level and an increase in reactive oxygen species (ROS) levels. In this context, two constitutive mitochondrial proteins, the adenine nucleotide translocator (ANT, inner membrane (IM)) and the voltage-dependent anion channel (VDAC, outer membrane (OM)), cooperate with the Bax and Bcl-2 proteins family. Bax is a pro-apoptotic cytosolic protein, which interacts with ligands, such as Bid and PUMA, activates and translocates to the mitochondrion to induce cell death. Furthermore, the ANT-Bax cooperation has been reported in several physiopathological models. These proteins belong to the mitochondrial permeability transition pore (PTPC), a multiprotein complex localized at the contact sites of the OM and IM membranes. The precise composition of this pore is still unknown but, several independent hypotheses converge to the possibility that ANT (IM) and VDAC (OM) interact to form a double channel. In normal conditions, this double channel opens transiently and mediates the channeling of ATP from the matrix (site of synthesis) to the cytosol (final destination). Upon stimulation by a wide range of endogenous as well as exogenous stimuli, PTPC opens as a high conductance channel to allow the free passage of water and metabolites of MM<1.5 kDa, inducing a matrix swelling and the subsequent rupture of the OM, thus facilitating the release of mitochondrial proteins into the cytosol. This model has been challenged by a publication in 2004 based on the generation of conditional double-knock out mice for ANT1 and ANT2 in the liver, two isoforms of ANT, suggesting that ANT could be dispensable for apoptosis (1). Nevertheless, a novel ANT isoform (ANT4) has been identified recently (2,3) and, as ANT represents the most abundant member of a large family of highly homologous members, i.e. the mitochondrial carriers, in the absence of ANT, another carrier might replace the functional role of ANT for the induction of MMP to compensate the absence of ANT1 and 2 (4,5).

Interestingly, Jang et al. (6) demonstrated that ANT2 suppression by vector-based siRNA inhibits tumour growth in in vivo human breast cancer models. This reveals the therapeutic potential of an ANT targeting approach in oncology. An attempt to target pharmacologically ANT has been previously undertaken, using the peptidic approach (7,8), and preliminary results revealed several technological difficulties, resulting from the fact that peptides cannot penetrate into the cell and need to be coupled with targeting sequences (e.g. Tat, Ant).

DETAILED DESCRIPTION

The inventors have now prepared ANT-targeted small molecules particularly for therapeutic applications. Medicinal chemistry approach coupled with in silico studies yield to several small organic compounds, which proved to be specific for ANT and fulfil druggability criteria (good cell penetration and biodisponibility).

Such molecules may have other cellular targets.

The invention thus relates to molecules particularly able to induce apoptosis or similar cell death mechanisms.

It also relates to those of the molecules which are new compounds.

According to another object, the invention relates to pharmaceutical compositions comprising said new molecules as active principles of drugs.

According to still another object, the invention relates to the use of said above molecules able to induce apoptosis for making drugs inducing apoptosis.

This is another aim of this invention to provide a method for inducing cell death by targeting the ADP/ATP translocator ANT in cellula.

The molecules used as ligands according to the invention have a substituted nitrogeneous heterocycle, designated by A, wherein A is a substituted pyrimidinone of formula I

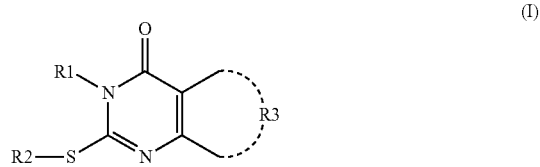

wherein
R1 is
—$(CH_2)_n$—CO—OH;
—$(CH_2)_n$—CO—OR;
—$(CH_2)_n$—CO—NHR;
—$(CH_2)_n$—CO—N(R,R');
—$(CH_2)_n$—OH;
—$(CH_2)_n$—OR;
—$(CH_2)_n$—OAr;
—$(CH_2)_n$—C(R,R')—$(CH_2)_n$—OH,
R and R', in the above radicals, being identical or different and representing H or a C1-C12 alkyl or cycloalkyl radical; and Ar is a phenyl or Het., Het. representing an heterocyclic radical with one or several hetero atoms selected between N, S and O, said phenyl or heterocycle being optionally substituted by one or several atoms, groups or radicals selected from halogen atoms such as Cl, Br, I, or halogenated groups such as —CCl$_3$ or —CF$_3$; one or several —OH, —OR, —COOH or —COOR groups; a phenyl; a linear or branched C1-C12 alkyl radical; —NH—COR; or —CN; said groups occupying the same or different positions on the phenyl or heterocyclic radical;

a linear or branched C1-C12 alkyl radical;
a linear or branched C2-C12 alkenyl radical;
—(CH$_2$)$_n$—C3-C6 cycloalkyl radical;
—(CH$_2$)$_n$Ar or —(CH$_2$)$_n$—Het.;
—(CH$_2$)$_n$—NH—CO—R;
—(CH$_2$)$_n$—NH$_2$;
—(CH$_2$)$_n$—N(R,R');
—(CH$_2$)$_n$—NH—CO—OH;
—(CH$_2$)$_n$—NH—CO—OR;
—NH—(CH$_2$)$_n$—CO—OH;
—NH—(CH$_2$)$_n$—CO—OR;

R2 is
—(CH$_2$)$_n$— Ar, Ar being such as above defined and being optionally substituted such as above defined;
a linear or branched C1-C12 alkyl or a linear or branched C2-C12 alkenyl radical;
—(CH$_2$)$_n$—OH;
—(CH$_2$)$_n$—OR;
—(CH$_2$)$_n$—CO—Het;
—(CH$_2$)$_n$—NH—CO—R;
—(CH$_2$)$_n$—NH$_2$;
—(CH$_2$)$_n$—N(R,R');
—(CH$_2$)$_n$—CO—OH;
—(CH$_2$)$_n$—CO—OR;
a linear or branched C1-C12 alkyl radical;
—(CH$_2$)$_n$—C(R)═CH—C(R)═CH$_2$, R3 forms a phenyl or an heterocyclic condensed group with the two adjacent carbons of the pyrimidinone residue, said condensed group being optionally substituted such as above defined for Ar and Het. and/or condensed to a cyclohexyl or oxanyl group, in turn optionally substituted such as above defined for Ar;

n is 0 or an integer from 1 to 5; or

A is a substituted pyrimidine of formula II

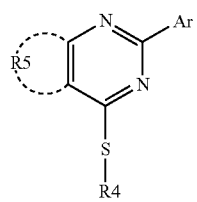

(II)

wherein
R$_4$ is a —CO—NH—Ar radical, optionally substituted such as above defined;
R$_5$ forms a phenyl or heterocyclic group condensed to the two adjacent carbon groups of the pyrimidine residue, said phenyl or heterocyclic group being optionally substituted such as above defined, and
Ar being such as above defined with respect to formula I or A is a substituted pyridine group of formula III

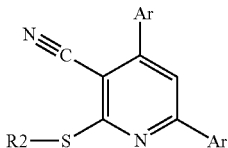

(III)

wherein,
Ar and R2 are as above defined with respect to formula I.

In a first family, preferred ligands have formula I wherein R3 forms a phenyl or a thienyl group with the pyrimidinone residue, said phenyl or thienyl group being optionally substituted such as above defined.

Advantageously,
R1 is selected from the group comprising —(CH$_2$)$_n$—CO—OH; a branched C1-C6 alkyl group; —(CH$_2$)$_n$—C3-C6 cycloalkyl group; —(CH$_2$)$_n$—NH$_2$; —(CH$_2$)$_n$—NH—CO—R; —(CH$_2$)$_n$Het., with Het. representing a pyridyl radical.

In more preferred derivatives of said first family, R1 and R3 are as above defined and R2 is a —(CH$_2$)$_n$— phenyl group, advantageously substituted by one or several C1-C3 alkyl groups or an halogen, particularly Cl.

Preferred derivatives have the following formulae

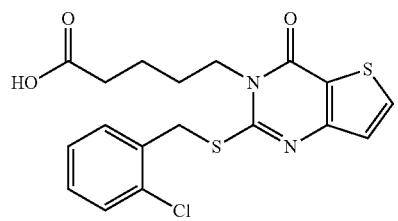

Compound 1

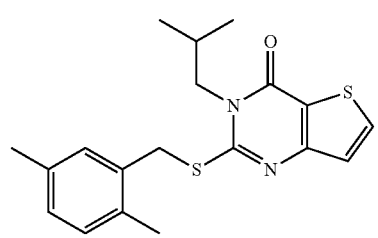

Compound 2

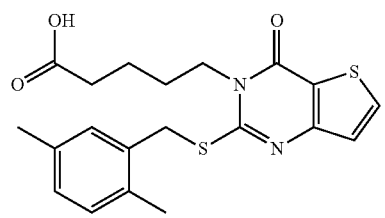

Compound 3

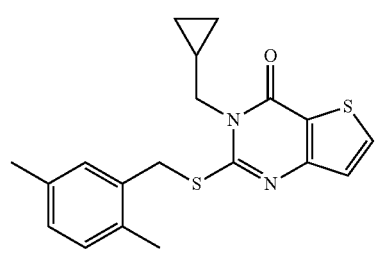

Compound 4

Compound 5
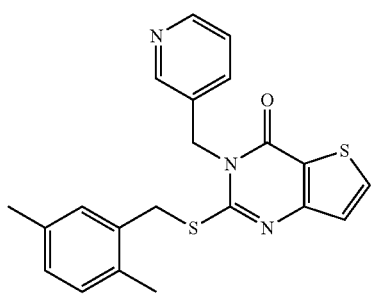
Compound 6
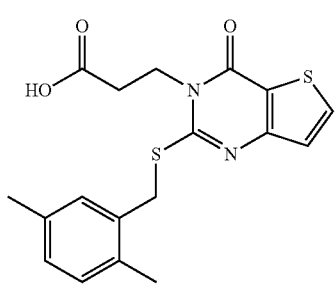
Compound 7
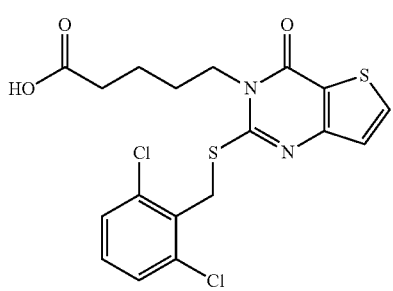
Compound 8
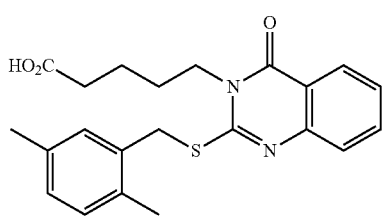
Compound 9
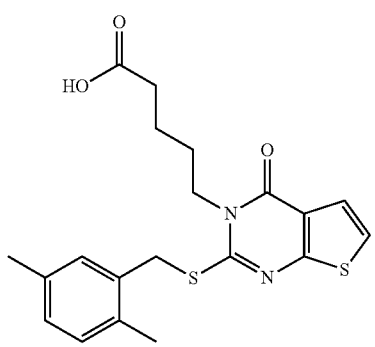
Compound 10
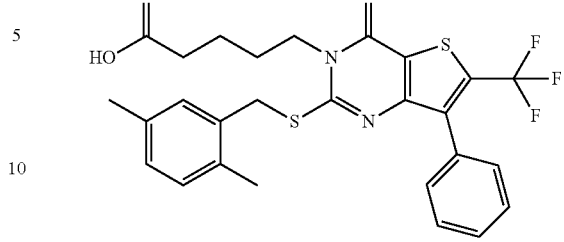
Compound 11
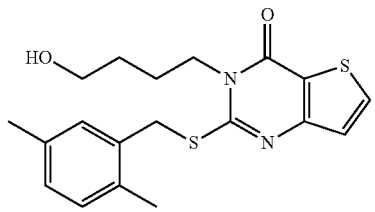
Compound 12
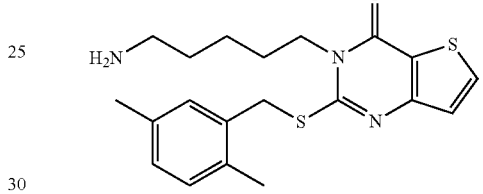
Compound 13
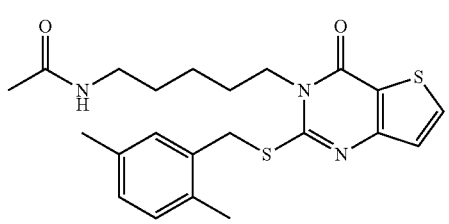
Compound 14
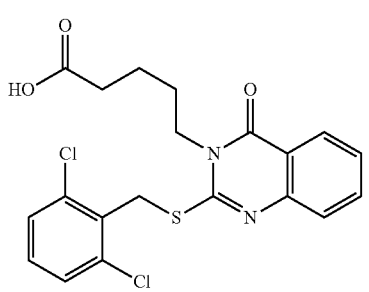
Compound 15
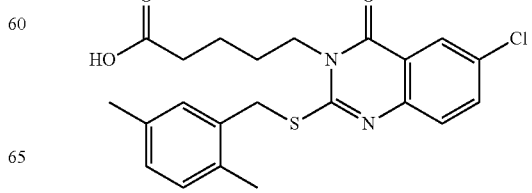

Compound 16

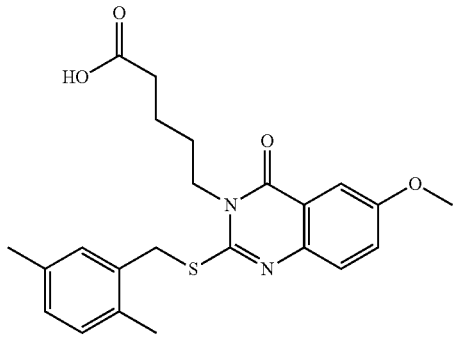

In a second family, preferred ligands have formula II wherein Ar and R4 are a phenyl group, advantageously substituted such as above defined with respect to formula I.

In more preferred derivatives R5 forms a phenyl group with the two adjacent carbon atoms of the pyrimidine residue or a thienyl group optionally condensed to a cyclohexyl or a oxanyl group, optionally substituted such as above defined with respect to Ar in formula I.

Preferred derivatives have the following formulae:

Compound 17

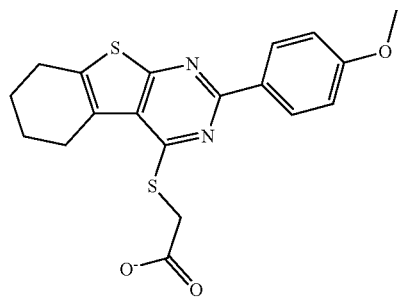

Compound 18

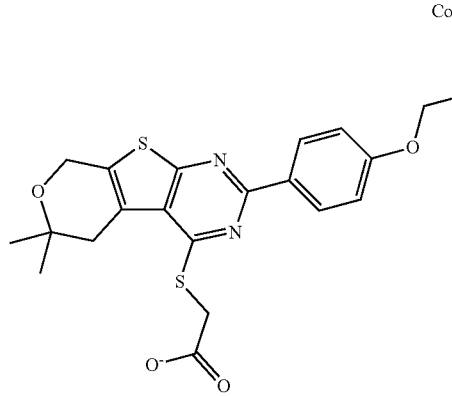

Compound 19

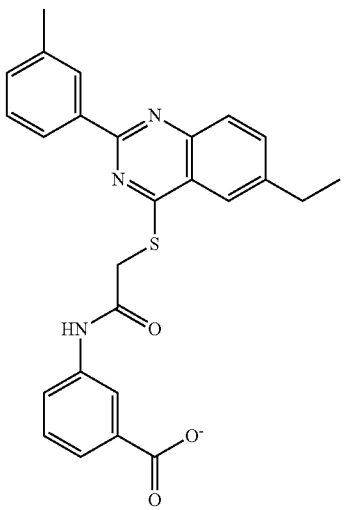

In a third embodiment of the invention preferred ligands have formula III, wherein both Ar are phenyl groups, optionally substituted such as above defined, and R2 is as above defined with respect to formula I, preferably a —(CH2)n-COOH group.

Preferred derivatives have the following formulae:

Compound 20

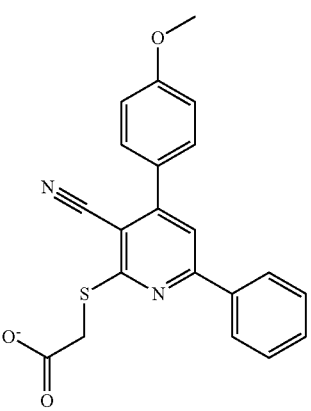

Compound 21

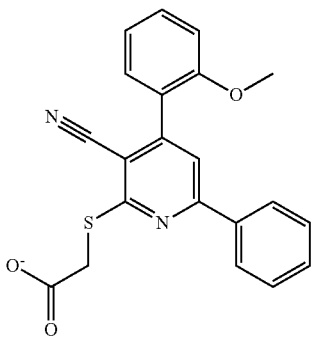

The invention also relates to the above defined derivatives as new products, the following compounds 1, 2, 17, 18, 19, 20 and 21 being excluded:

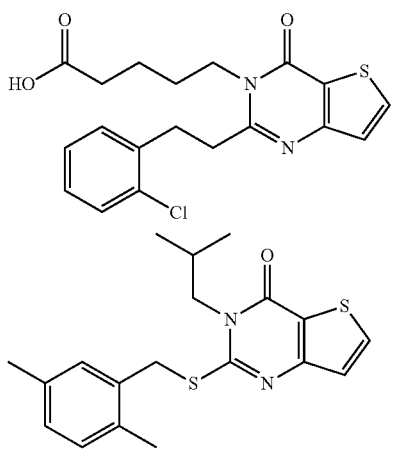
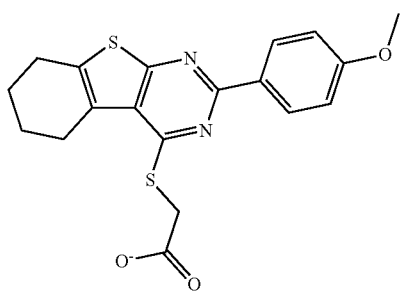
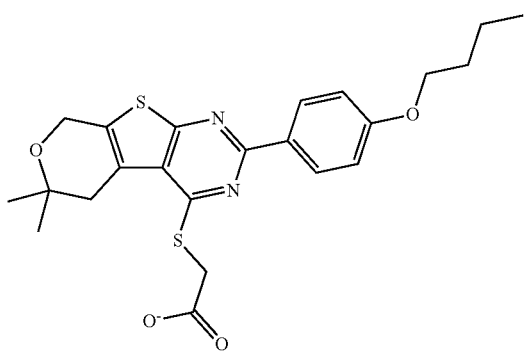
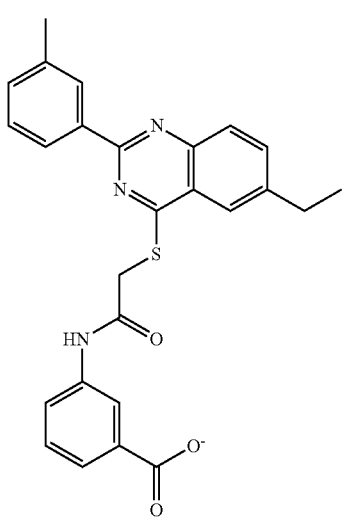
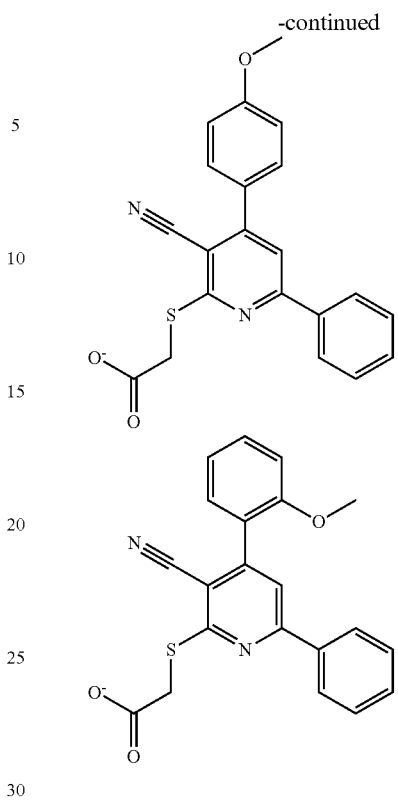

More particularly, taking advantage of the published crystal structure of bovine ANT1 with its specific inhibitor carboxyatractyloside (9) (FIG. 1A), the inventors have identified by molecular docking a library of putative ANT-ligands in silico. Considering the high homology between bovine ANT1 and human ANT isoforms in term of tertiary structure, a three-dimensional analysis permitted (1) to localize the carboxyatractyloside, a well-known inhibitor of ADP/ATP translocation, in the human ANT2 binding pocket (FIG. 1B) and (2) to identify chemical structures able to interact similarly with amino acid residues of the ANT binding pocket.

The library is constituted of a total of 1171 small commercial molecules among which 956 have been tested. Each compound has been evaluated on the following in vitro screening assays: HT-29 and BxPC3 tumour cells lines viability and ADP/ATP translocator activity of ANT on isolated mitochondria. These screening techniques lead to selection of molecules being efficient ANT inhibitors with important cellular effects (cell death or growth delay).

Among them, compound 1 induces dissipation of the mitochondrial trans-membrane potential and apoptosis hallmarks that are abolished by caspase inhibitors (FIG. 3) and pro-apoptotic factors (Bax/Bak) deletion. Interestingly compound 1 is not cytotoxic for all cellular types. Indeed, the Wi-38 cells express the ANT3 isoform as HT-29 and BxPC3, while the ANT2 isoform is almost no detectable (FIG. 4A). In correlation with ANT expression levels, compound 1 toxicity on normal lung fibroblasts is minor compared to tumor cells (HT-29, BxPC3) (FIG. 4B). On lymphocytes (PBMC, not shown), the compound presents no sign of toxicity for doses below 400 µM.

The importance of ANT isoforms in cytotoxic effects of the selected ANT-ligands has been evaluated using *S. cerevisiae* strains deficient for ANT isoforms (FIG. 5). Clonogenic assays on these strains are used to ensure that cytotoxic effects of the ANT-ligands are really due to the expression of ANTs in the cells.

The inventors found that the strain deficient for ANT isoforms (ΔANT1, 2 & 3) is more resistant to the compound 1 than the wild-type (WT) control strain, indicating that the mechanism of cell death induced by this ligand is ANT-dependent (FIG. 5).

For the first time, it is possible to demonstrate that an ANT-ligand induces cell death by targeting the ADP/ATP translocator ANT in cellula. Structure/activity relationship studies lead to the optimization of the compound in terms of killing efficiency and selectivity for one of the ANT isoforms (FIG. 6). The chemical structures of optimized compound 1 derivatives are given in FIG. 7.

The invention also relates to a method for inducing cell death by targeting the ADP/ATP translocator ANT in cellula comprising adding an effective amount of at least one of the above defined derivatives.

The above defined molecules are advantageously used as active principle of drugs.

The invention thus also relates to pharmaceutical compositions comprising a therapeutically effective amount of at least one of the above defined molecules in association with a pharmaceutically acceptable carrier.

Said compositions are administrable by the appropriate way, comprising oral, parenteral (subcutaneous, intravenous), injectable and topical including intratumoral ways of administration.

They are advantageously formulated as liquid solutions with appropriate carriers and/or diluents and/or solvents.

The pharmaceutical compositions of the invention may further comprise a therapeutic agent selected in the group comprising chemotherapeutics, apoptosis modulators, antimicrobial, antiviral, antifungal or anti-inflammatory agents.

The above defined pharmaceutical compositions are useful for cancer therapy.

The invention also relates to the use of a ligand such as above defined for making a proapoptotic drug for treating cancer.

Therapeutically effective amount of the compounds will advantageously be 0.1 mg/kg to 100 mg/kg body weight with a daily to weekly administration.

The invention also relates to a method for the synthesis of the above defined ligands.

The derivatives of formula I are thus preferably obtained by reacting a derivative of formula IV

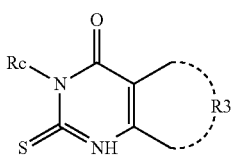
(IV)

wherein Rc is R1 such as above defined or a —(CH$_2$)$_n$—O—Si(CH$_3$)$_2$—C(CH$_3$)$_3$ or —(CH$_2$)$_n$—NH—C(=O)—O—C(CH$_3$)$_3$ radical and R3 is as above defined, with a derivative of formula V

R2-R''  (V)

wherein R2 is as above defined and R'' is a reactive group such as a halogen. Preferably, R'' is Cl. or Br.

Said reaction is advantageously carried out in the presence of triethylamine in an organic solvent. Appropriate solvents comprise DMF (dimethylformamide) and DCM (dichloromethane).

When Rc comprises a —OH terminal group, the reaction is followed by a chromatography on a Dowex type column to recover the desired derivative.

When Rc comprises a —NH2 terminal group, the resulting derivative is treated with TFA and DCM. Said derivative, by reaction with Rc(=O) R'', may be used to obtain derivatives of formula I with R1=-(CH2)n-NH—C(=O)—R, R and R'' being such as above defined.

According to the invention, the derivatives of formula IV are obtained by reacting a derivative of formula VI

(VI)

wherein S=C=N— and —C(=O)— OR are on carbon adjacent positions on Ar and R is such as above defined, with an amino derivative of formula VII

(VII)

with R1 being such as above defined.

Said reaction is advantageously carried out in an alcoholic solvent and H2O. Preferably the alcoholic solvent is isopropanol.

The compounds of the second and third families are obtained according to usual synthesis routes, advantageously using commercially available molecules as starting materials.

Other characteristics and advantages are given in the following examples which refer to FIGS. 1 to 8, wherein:

FIG. 1: Illustrates in silico molecular docking to find new ANT-ligands (A) Structure of the carboxyatractyloside (CAT)-bovine ANTI complex (adapted from (26))

(B) Prediction by computer analysis of the carboxyatractyloside (CAT) localization in the human ANT2 binding.

Figure 2:
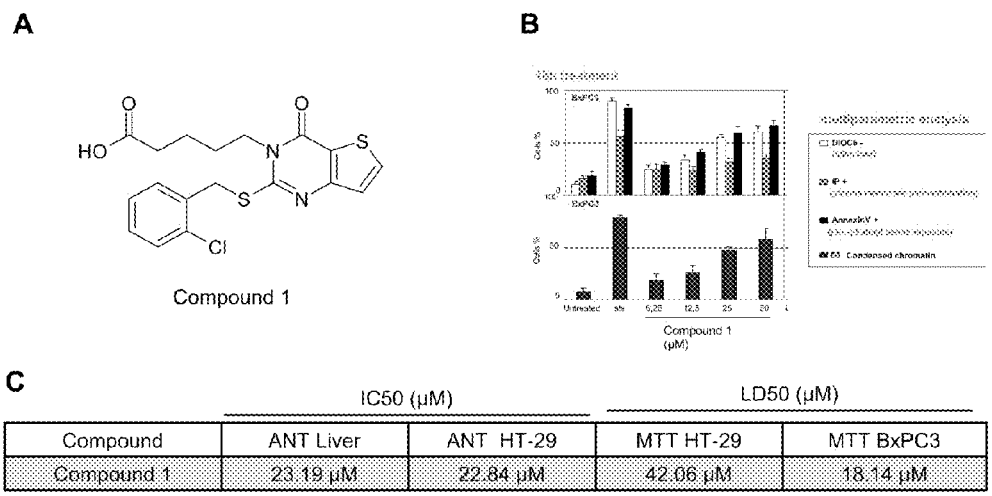

FIG. 2: The ANT-ligand is pro-apoptotic on HT-29 and BxPC3 tumor cell lines (A) Chemical structure of compound 1

(B) Multiparametric analysis (chromatin condensation, mitochondrial transmembrane potential (ΔΨm) loss, plasma membrane permeabilization, phosphatidylserine exposure) of cellular effects of the ANT-ligand on BxPC3 cell line after 48 h treatment.

(C) Effects of compound 1 on ADP/ATP translocator activity of ANT measured on isolated mitochondria from mice liver or HT-29 tumor cell line (IC50 is given in μM based on ANT assays) and on viability of HT-29 and BxPC3 tumor cell lines (LD50 is given in μM based on MTT assays at 48 h).

Figure 3:
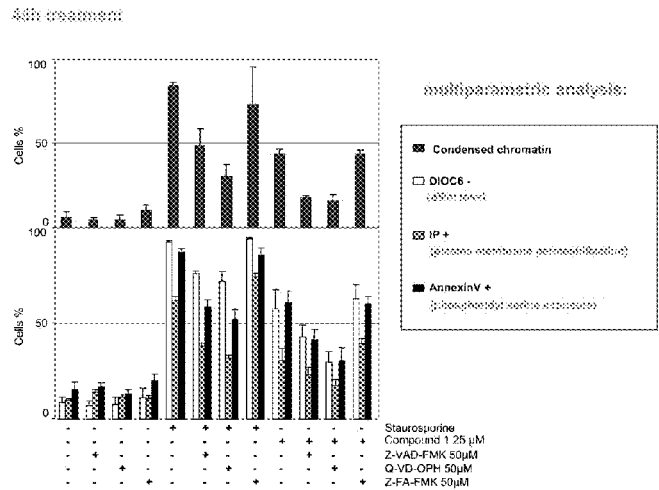

FIG. 3: Compound 1 induced-cell death is caspase-dependent

Compound 1 induces classical hallmarks of apoptosis: mitochondrial potential (ΔΨm) loss (Dioc6−), phosphatidylserine exposure (Annexin-V+), plasma membrane permeabilization (PI+) and chromatin condensation as shown by multiparametric analysis. Apoptosis induced by the ANT-ligand is inhibited by pan-caspase inhibitors (z-VAD-fmk, Q-VD-OPH) but not by the cathepsin B inhibitor (Z-FA-fmk).

Figure 4:
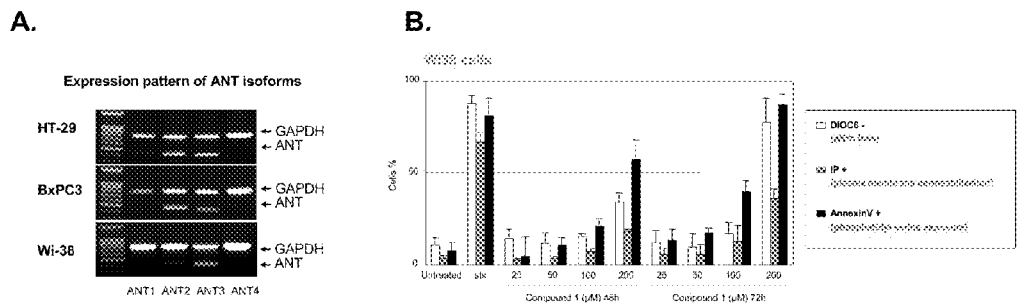

FIG. 4: Compound 1 induces low toxicity on normal fibroblast Wi-38

(A) Expression pattern of ANT isoforms in HT-29, BxPC3 and Wi-38 (normal lung fibroblasts) cell lines after RT-PCR reaction on total RNA (B) Multiparametric analysis (mitochondrial transmembrane potential, plasma membrane permeabilization, phosphatidylserine exposure) of cellular effects of the ANT-ligand on Wi-38 cell line after 48 h and 72 h treatments.

FIG. 5: Target validation of compound 1 using ANT-deficient yeasts (A) Quantitative estimation of yeasts viability at 48 h after 2 h incubation with compound 1

(B) Illustration of WT (W303) and JL1-3 (ΔANT1, 2 and 3) yeast strains growth on plates at 48 h after 2 h incubation with compound 1.

FIG. 6: Optimization by structure-Activity Relationship studies

The table shows the effects of optimized compounds on HT-29, BxPC3, MiaPaca, Wi-38 cell viability (LD50 in µM); on ANT activity in mice liver and HT-29 tumor cell line mitochondria (IC50 in µ); on swelling (DS50 in µM) and ΔΨm parameters (DP50 in µM) in mice liver mitochondria (Mitotrust™ platform); and on viability of wild-type (W303) and ANT-deficient (JL1-3) yeasts strains (ED50 in µM).

Figures 7, 8:
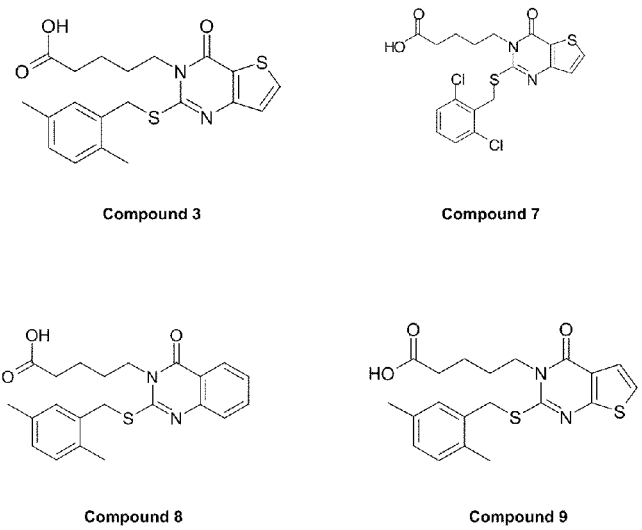

FIG. 7: Chemical structures of optimized compounds in structural family 1.

FIG. 8: Effects of compounds (family 2 & 3) on cell lines and isolated mitochondria The table shows the effects of compounds on HT-29, BxPC3, MiaPaca, Wi-38 cell viability (LD50 in µM); on ANT activity in mice and HT-29 tumor cell line mitochondria (EC50 in µM); on swelling (DS50 in µM) and ΔΨm parameters (DP50 in µM) in mice liver mitochondria.

ADP/ATP TRANSLOCASE ACTIVITY ASSAY

The ANT activity assay is an indirect measure of ATP translocation from isolated mitochondria in exchange of ADP followed by NADPH formation in the medium. This assay is using a complex system of ATP detection constituted of enzymes (hexokinase, glucose-6-phosphate-dehydrogenase), a substrate (glucose) and a co-substrate (NADP+) allowing NADP+ reduction in NADPH. The method is adapted from (10), with modifications: reactions in microplates, no pre-loading of mitochondria with ATP, detection of NADP+ reduction by fluorescence (Spectrofluorimeter Infinite M200, Técan), incorporation of AP5A (P1P5-diadenosine-5'-pentaphosphate) to inhibit the adenylate kinase-dependent ATP synthesis (IC50: dose inducing 50% of carboxyatractyloside inhibition activity).

Viability Assay and Characterisation of Cell Death

MTT assay was used to evaluate the viability of a large range of human cell lines in presence of small molecules. Dose-response experiments allow us to determine a lethal-dose 50 ($LD_{50}$; dose killing 50% of the cellular population) for each compound on a particular cell type after a 48-hour incubation. This viability assay is used as a first screening assay to Identify cell-permeant molecules able to include cell death (cytotoxic) or growth delay (cytostatic) among the 956 molecules of the ANT-ligands library. We have chosen to select molecules having an $LD_{50}$ below 50 µM on HT-29 (colon adenocarcinoma) or BxPC3 (pancreatic adenocarcinoma) cell lines. These molecules come into the ANT activity screening assays and the efficient ANT-inhibitors (IC50 below 50 µM) are investigated for their mechanisms of cell death induction. Indeed, the characterization of cell death consists in a multiparametric analysis of treated-cells by flow cytometry (FacsCalibur, Becton Dickinson) where can be measured (1) the loss of mitochondrial trans-membrane potential (Δψm DIOC6 labelling), (2) the plasma membrane permeabilization (Propidium Iodide labeling) and (3) the phosphatidylserines exposure (Annexin-V-fitc labelling).

Scheme of Synthesis of Compounds 1-6 and 8-16

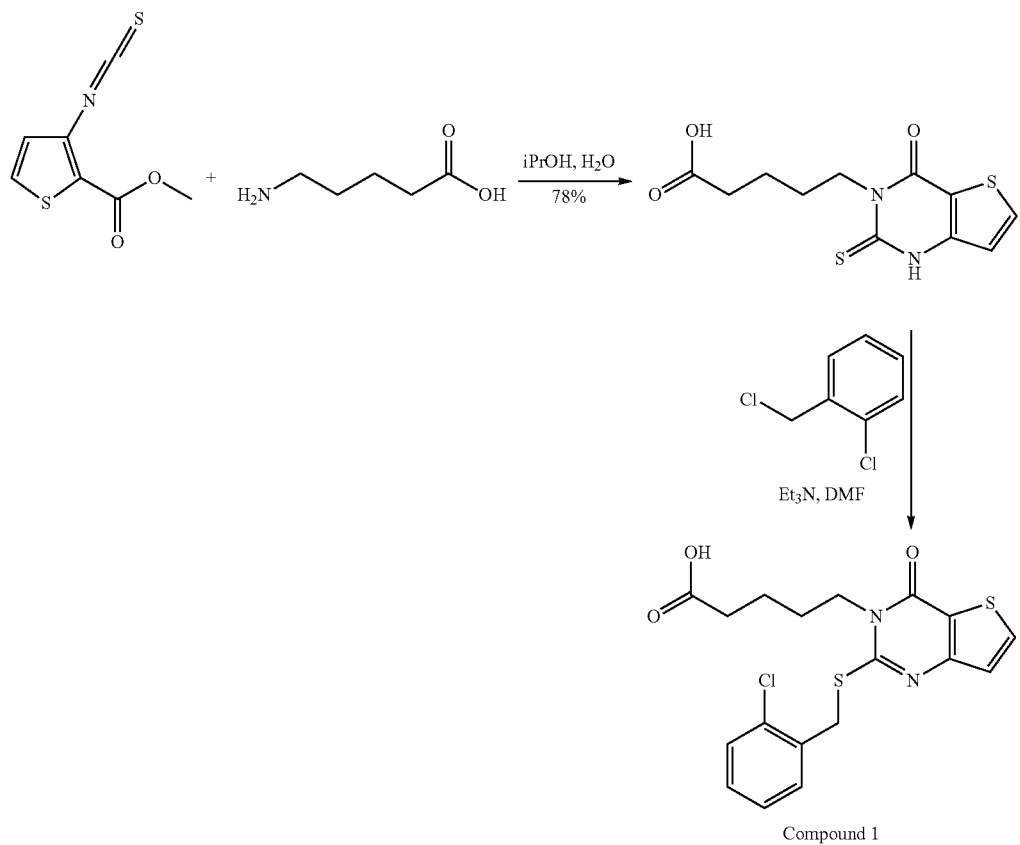

Compound 1

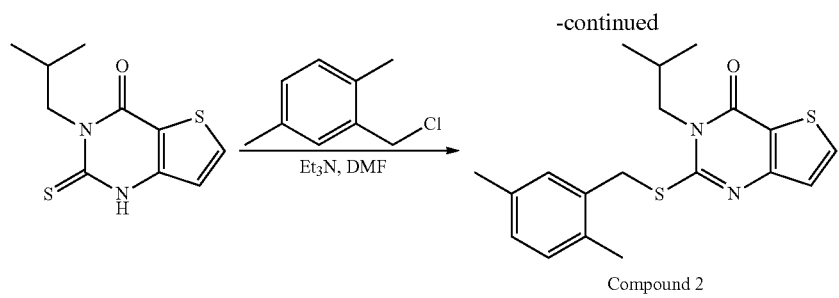
Compound 2
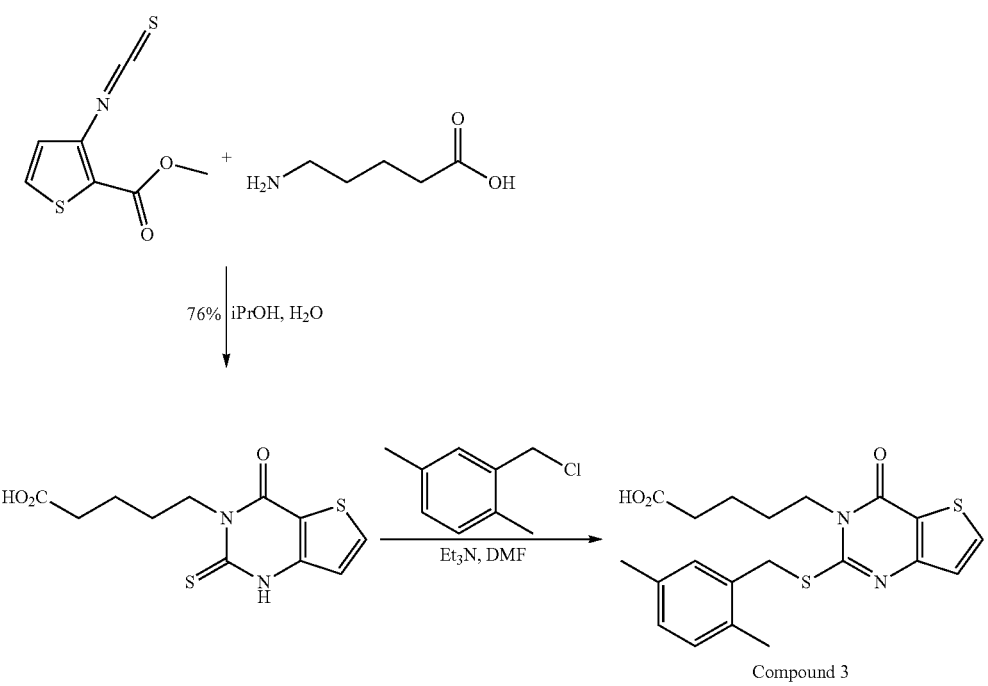
Compound 3
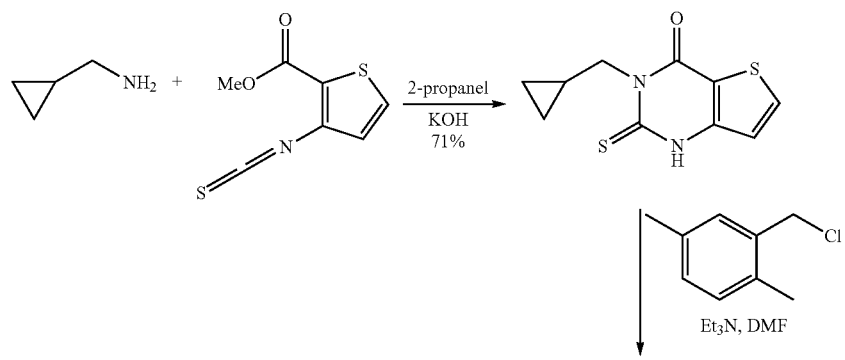
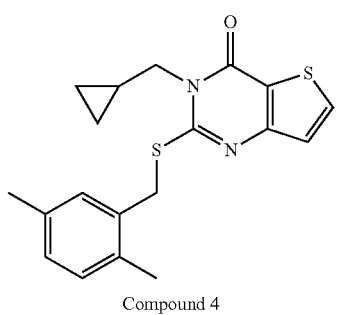
Compound 4

-continued
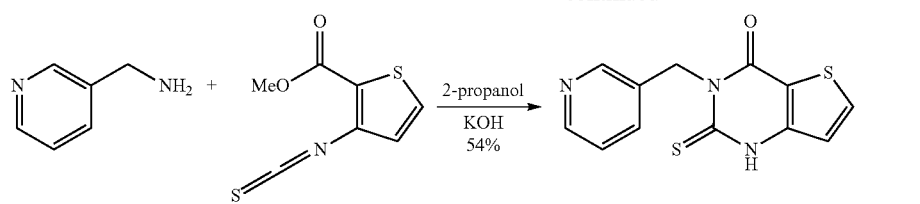
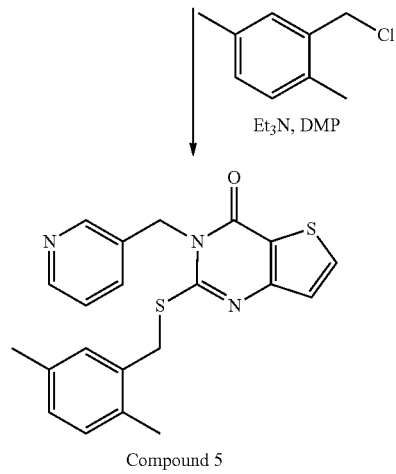
Compound 5
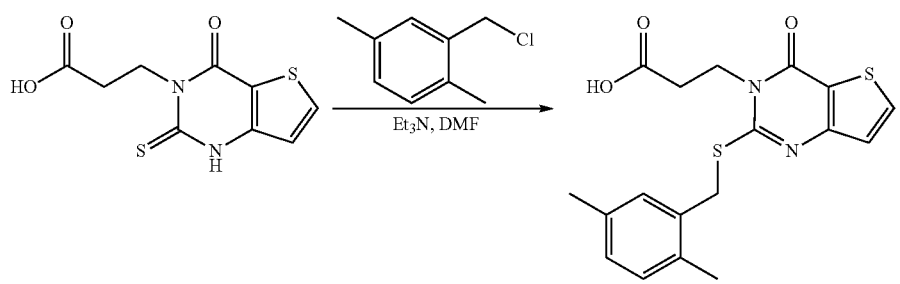
Compound 6
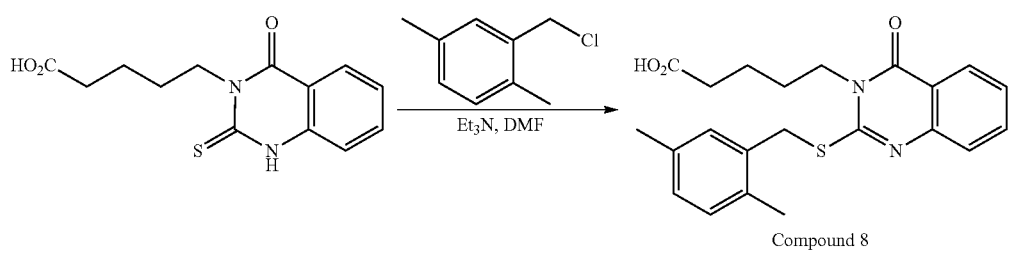
Compound 8
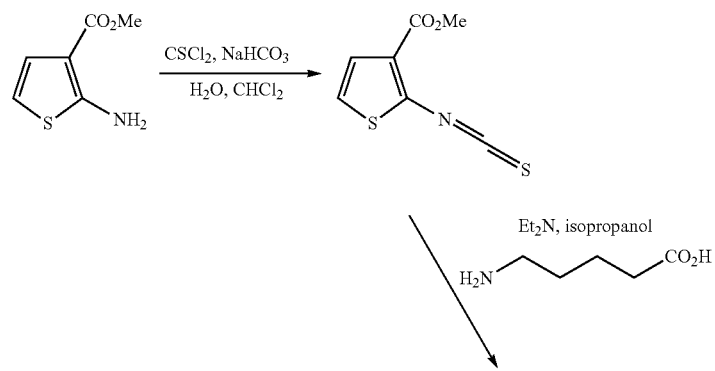

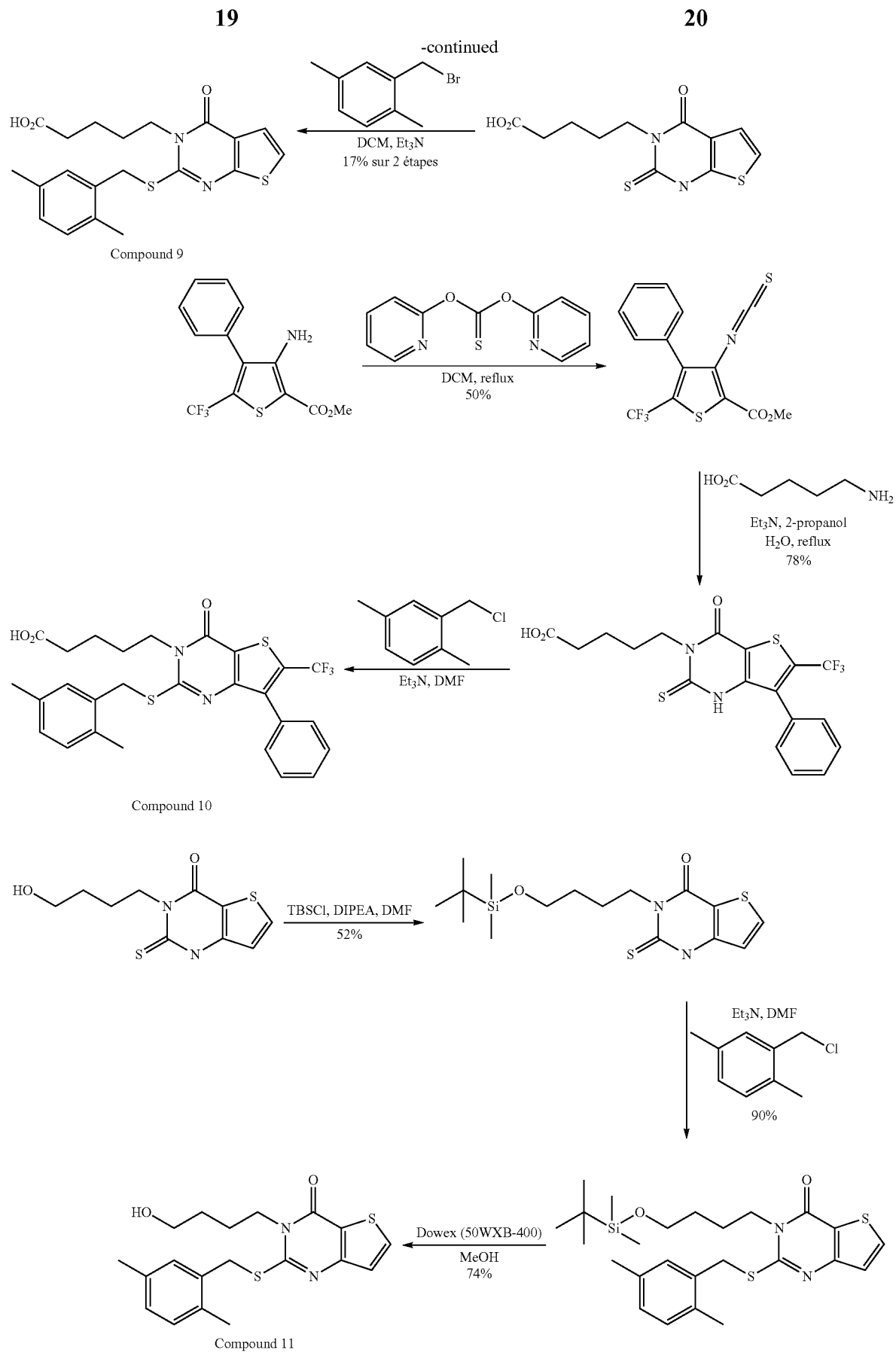

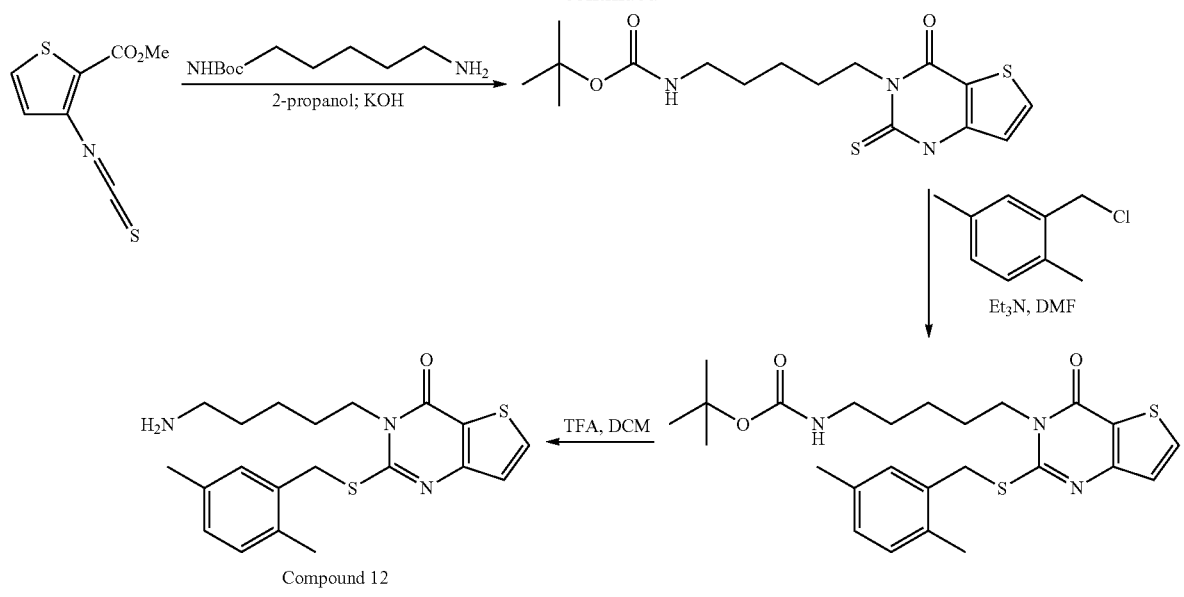
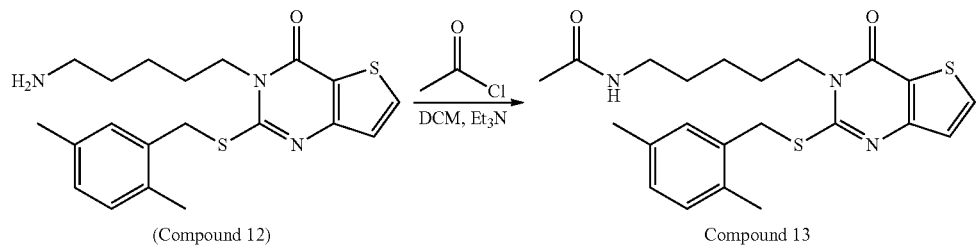
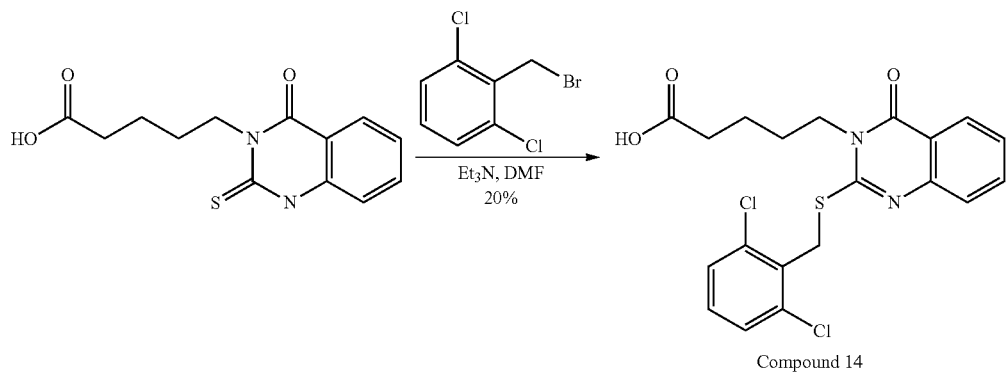
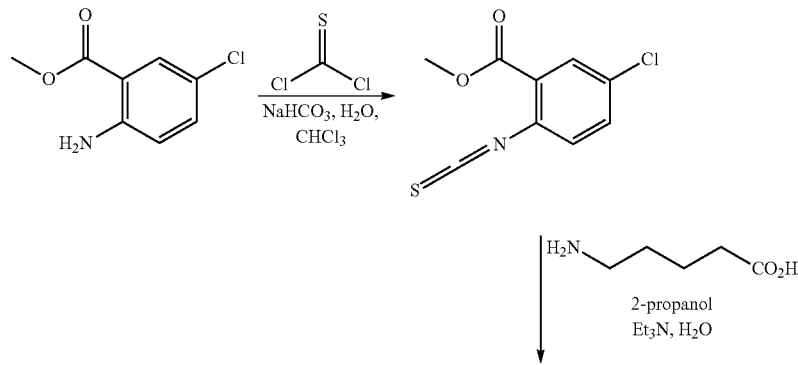

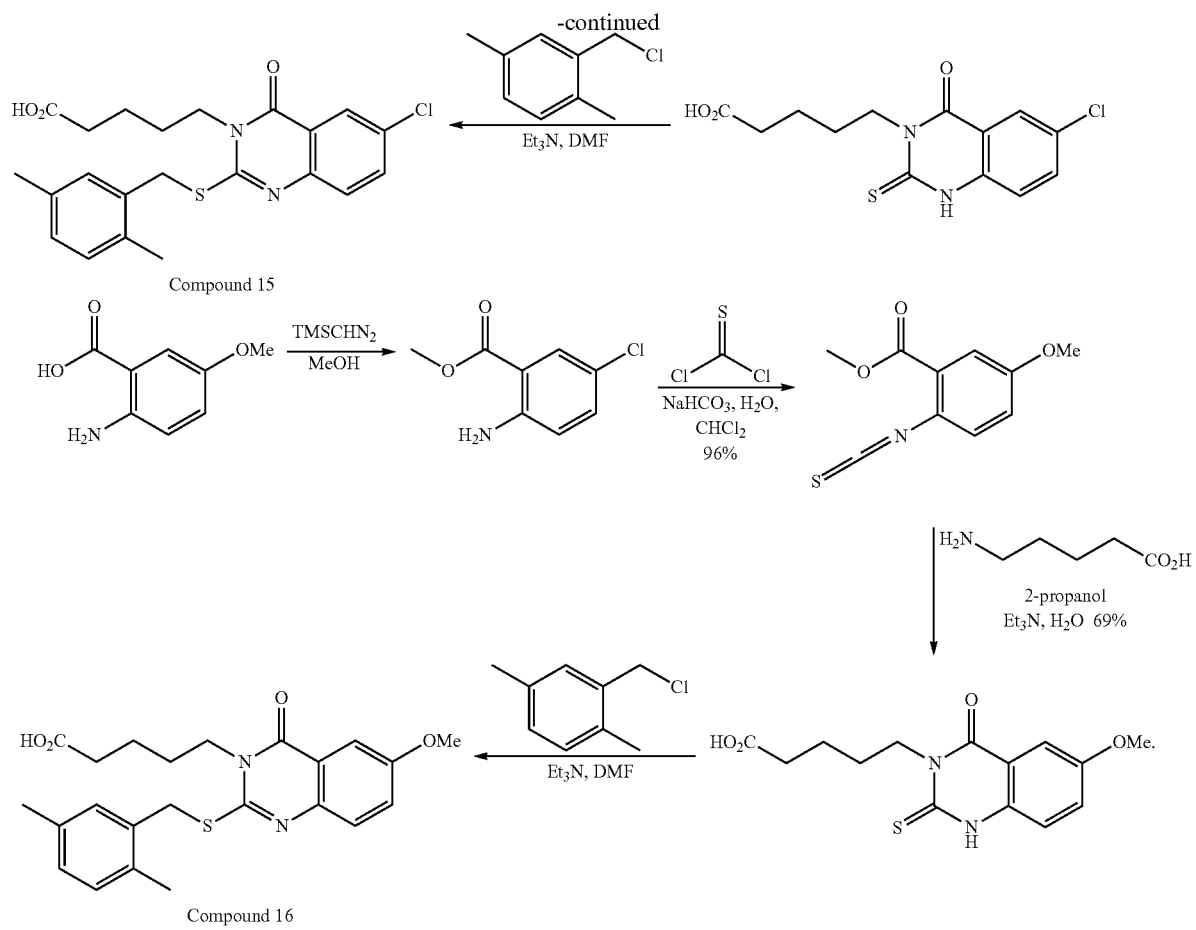

Compound 15

Compound 16

BIBLIOGRAPHIC REFERENCES

1. Dolce, V., Scarcia, P., Iacopetta, D., and Palmieri, F. (2005) *FEBS Lett* 579 (3), 633-637
2. Rodic, N., Oka, M., Hamazaki, T., Murawski, M., Jorgensen, M., Maatouk, D., Resnick, J., Li, E., and Terada, N. (2005) *Stem Cells* 23, 1314-1323
3. Halestrap, A. (2005) *Nature* 434 (7033), 578-579
4. Jacotot, E., Ravagnan, L., Loeffler, M., Ferri, K. F., Vieira, H. L., Zamzami, N., Costantini, P., Druillennec, S., Hoebeke, J., Briand, J. P., Irinopoulou, T., Daugas, E., Susin, S. A., Cointe, D., Xie, Z. H., Reed, J. C., Rogues, B. P., and Kroemer, G. (2000) *J Exp Med* 191 (1), 33-46
5. Jacotot, E., Ferri, K. F., El Hamel, C., Brenner, C., Druillennec, S., Hoebeke, J., Rustin, P., Metivier, D., Lenoir, C., Geuskens, M., Vieira, H. L., Loeffler, M., Belzacq, A. S., Briand, J. P., Zamzami, N., Edelman, L., Xie, Z. H., Reed, J. C., Rogues, B. P., and Kroemer, G. (2001) *J Exp Med* 193 (4), 509-520.
6. Jang, J. Y., Choi, Y., Jeon, Y. K., and Kim, C. W. (2008) *Breast Cancer Res,* 10, R11
7. Jacotot, E., Deniaud, A., Borgne-Sanchez, A., Briand, J., Le Bras, M., and Brenner, C. (2006) *Biochim. Biophys. Acta* 1757, 1312-1323
8. Deniaud, A., Hoebeke, J., Briand, J., Muller, S., Jacotot, E., and Brenner, C. (2006) *Curr Pharm Des,* 12, 4501-4511
9. Pebay-Peyroula, E., Dahout-Gonzalez, C., Kahn, R., Trezeguet, V., Lauquin, G., and Brandolin, G. (2003) *Nature* 426, 39-44
10. Passarella, S., Ostuani, A., Atlante, A., and Quagliariello, E. (1988) *Biochem Biophys Res Commun,* 156, 978-986

The invention claimed is:

1. An ANT ligand comprising a compound having the following formula

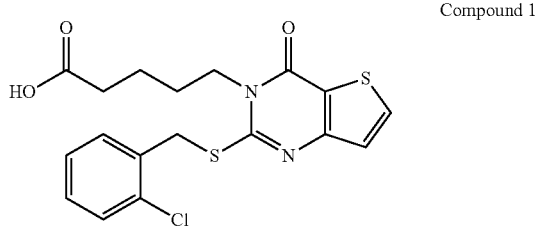

Compound 1

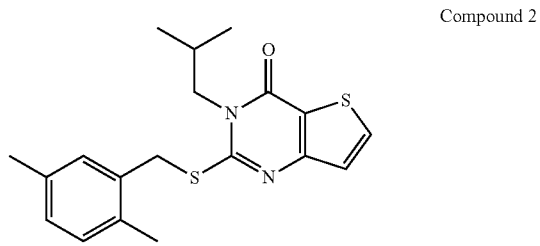

Compound 2

-continued
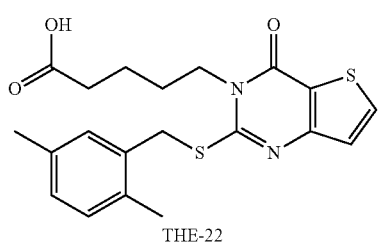
THE-22
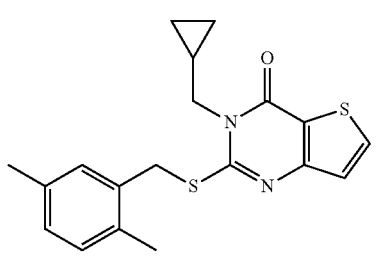
THE-25
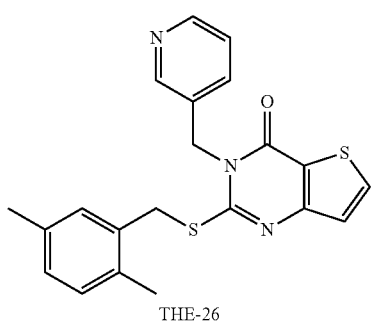
THE-26
Compound 6
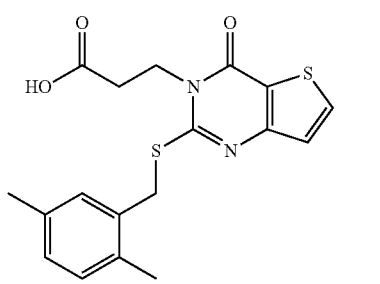
Compound 7
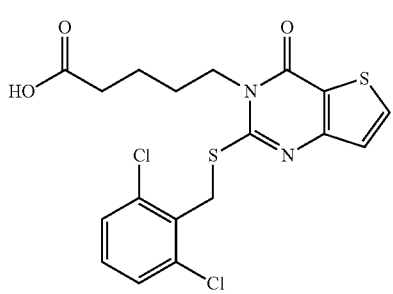
Compound 8
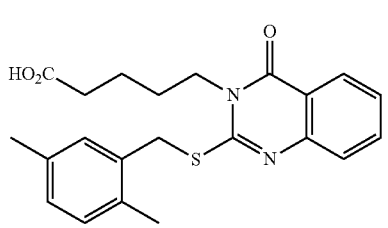
-continued
Compound 9
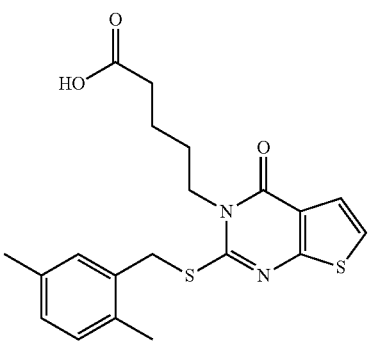
Compound 10
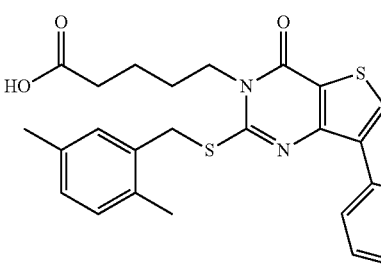
Compound 11
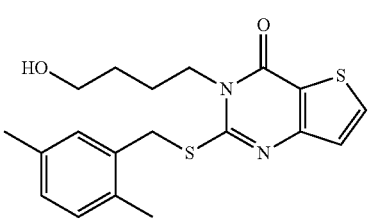
Compound 12
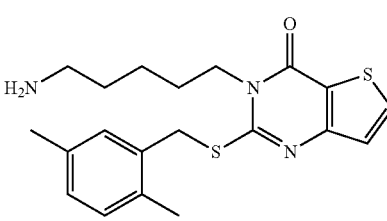
Compound 13
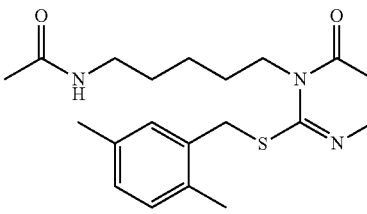
Compound 14

-continued
Compound 15
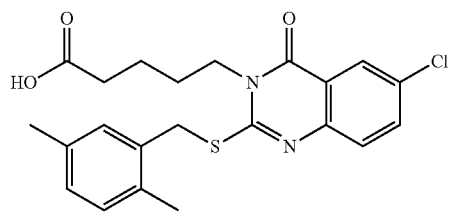
Compound 16
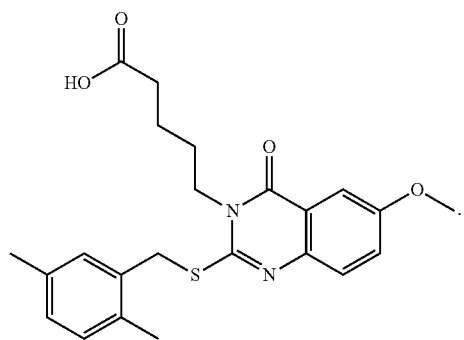
* * * * *